(12) United States Patent
Nairne et al.

(10) Patent No.: US 9,085,518 B2
(45) Date of Patent: Jul. 21, 2015

(54) METHOD FOR THE SYNTHESIS OF 18F-LABELLED MOLECULES

(71) Applicant: GE HEALTHCARE LIMITED, Buckinghamshire (GB)

(72) Inventors: Robert James Domett Nairne, Amersham (GB); Rajiv Bhalla, St. Lucia Brisbane (AU); Imtiaz Khan, Amersham (GB); Jane Brown, Amersham (GB); Anthony Wilson, Waddesdon (GB); Andres Black, Reading (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 14/351,741

(22) PCT Filed: Oct. 15, 2012

(86) PCT No.: PCT/EP2012/070401
§ 371 (c)(1),
(2) Date: Apr. 14, 2014

(87) PCT Pub. No.: WO2013/053941
PCT Pub. Date: Apr. 18, 2013

(65) Prior Publication Data
US 2014/0243555 A1    Aug. 28, 2014

Related U.S. Application Data

(60) Provisional application No. 61/547,091, filed on Oct. 14, 2011.

(30) Foreign Application Priority Data

Oct. 14, 2011   (GB) .................................. 1117785.4

(51) Int. Cl.
| | | |
|---|---|---|
| C07C 319/20 | (2006.01) | |
| C07B 59/00 | (2006.01) | |
| C07C 319/14 | (2006.01) | |
| C07C 227/16 | (2006.01) | |
| C07C 303/30 | (2006.01) | |
| C07D 451/02 | (2006.01) | |
| A61K 51/04 | (2006.01) | |
| C07C 67/10 | (2006.01) | |
| B01L 3/00 | (2006.01) | |

(52) U.S. Cl.
CPC ........... C07C 319/20 (2013.01); A61K 51/0406 (2013.01); A61K 51/0448 (2013.01); B01L 3/52 (2013.01); C07B 59/001 (2013.01); C07C 67/10 (2013.01); C07C 227/16 (2013.01); C07C 303/30 (2013.01); C07C 319/14 (2013.01); C07D 451/02 (2013.01); C07B 2200/05 (2013.01)

(58) Field of Classification Search
CPC .. C07C 319/20; C07C 319/24; C07C 227/16; C07C 303/30; C07C 67/00
USPC .................................. 564/238; 422/527, 554
See application file for complete search history.

(56) References Cited

U.S. PATENT DOCUMENTS

| | | | | |
|---|---|---|---|---|
| 7,432,397 | B2 * | 10/2008 | Brady et al. ................... | 564/238 |
| 8,058,311 | B2 * | 11/2011 | Robins et al. .................. | 514/634 |
| 2010/0113763 | A1 | 5/2010 | Moon et al. | |
| 2010/0143252 | A1 | 6/2010 | Robins | |
| 2011/0028725 | A1 | 2/2011 | Lim | |

FOREIGN PATENT DOCUMENTS

WO    2006/136846    12/2006

OTHER PUBLICATIONS

Wilson, et.al., Applied Radiation and Isotopes, vol. 46, No. 8, Aug. 1, 1995 pp. 765-770.
Zhang, et.al. Applied Radiation and Isotopes vol. 57, No. 3, Sep. 1, 2002 pp. 335-342.
Wang, et.al. Journal of Radioanalytical and Nucleare Chemistry, vol. 270, No. 2, Nov. 1, 2006 pp. 439-443.
Lundkvist, et.al. Nuclear Medicine and Biology, vol. 24, No. 7, Oct. 1, 1997 pp. 621-627.
Sang, et.al., European Journal of Nuclear Medicine and Molecular Imaging, vol. 34, No. 9, Mar. 24, 2007 pp. 1406-1409.
Robins, et.al. Bioorganic and Medicinal Chemistry Letter,s Vo. 20 (5) 2010 pp. 1749-1751.
Chaly, et.al. Applied Radiation and Isotopes vol. 51, 1999, pp. 299-305.

* cited by examiner

*Primary Examiner* — Shailendra Kumar
(74) *Attorney, Agent, or Firm* — Parks Wood LLC

(57) ABSTRACT

The present invention provides a method for the synthesis of 18F-labelled biomolecules, which is amenable to automation. The present invention also provides a cassette for automating the method of the invention. The method of the present invention provides numerous advantages over the prior art methods. One less purification step is required as compared with known methods. Also, in a preferred embodiment, one less reagent is required as a particular reagent is employed in two different steps. The chemistry process is thereby simplified, the cost of goods is reduced and the burden of validation and documentation of reagents required for GMP clinical production is minimized.

15 Claims, 2 Drawing Sheets

METHOD FOR THE SYNTHESIS OF 18F-LABELLED MOLECULES

This application is a filing under 35 U.S.C. 371 of international application number PCT/EP2012/070401, filed Oct. 15, 2012, which claims priority to Great Britain application number 1117785.4 filed Oct. 14, 2011 and to U.S. application No. 61/547,091 filed Oct. 14, 2011, the entire disclosure of which is hereby incorporated by reference.

TECHNICAL FIELD OF THE INVENTION

The present invention relates to the field of radiopharmaceuticals, and in particular to the preparation of compounds suitable for use in positron emission tomography (PET). A method for the synthesis of compounds labelled with $^{18}F$ is provided, which is preferably an automated method. Also provided by the present invention is a cassette suitable for carrying out the automated method of the invention.

DESCRIPTION OF RELATED ART

Due to its physical and chemical properties, $^{18}F$ is a preferred radionuclide for use in positron emission tomography (PET) tracers. The chemical reactions used to incorporate $^{18}F$ into organic molecules can be broadly divided into two categories, namely nucleophilic and electrophilic reactions. For nucleophilic fluorination, [$^{18}F$]-fluoride ion ($^{18}F^-$) is used as the source of $^{18}F$. It is normally obtained as an aqueous solution from the nuclear reaction $^{18}O(p,n)^{18}F$. Once it is made reactive by the addition of a cationic counterion and the removal of water $^{18}F^-$ can be reacted with a compound comprising a suitable leaving group so that $^{18}F$ becomes incorporated into the compound in place of the leaving group. Suitable leaving groups include Cl, Br, I, tosylate (OTs), mesylate (OMs), nosylate (ONs) and triflate (OTf). The $^{18}F$-labelled compound obtained can either be the final product, or is an $^{18}F$-labelled synthon that is used as a labelling reagent to obtain the final product. An example of such a synthon is $^{18}F-(CH_2)_x$-LG wherein LG represents a leaving group, which can be used to alkylate thiol, hydroxy, or amine groups in a precursor compound to result in an $^{18}F$-labelled product. In order for the alkylation reaction to proceed successfully, deprotonation of the thiol, hydroxy, or amine group is necessary and as such the reaction is typically carried out in the presence of a base.

$^{18}F$-labelled radiotracers are at present conveniently prepared by means of an automated radiosynthesis apparatus. There are several commercially-available examples of such apparatus. An apparatus such as FASTlab™ (GE Healthcare) comprises a disposable cassette in which the radiochemistry is performed, which is fitted to the apparatus to perform the radiosynthesis. In order for a radiofluorination reaction to be carried out on such an automated synthesis apparatus, it is necessary for each of the reagents to be soluble in order to be transported around the device. In addition, a separate vial is required for each reagent and it is desirable for there to be as few vials as possible in order to simplify the chemistry process, reduce the cost of goods and simplify or minimise the burden of validation and documentation of reagents required for GMP clinical production.

Radiolabelled alkylthiophenyl-guanidine compounds and their potential applications in imaging central nervous system receptors have been reported in WO 2006/136846 and by Zhao et al (J Label Compd Radiopharm, 2006; 49: 163-70). It has been demonstrated that these compounds have high affinity for N-methyl-D-aspartate (NMDA) receptors (<5 nM) and have potential utility for the diagnosis of NMDA-mediated disorders such as epilepsy, stroke, neuropathic pain and schizophrenia.

The manual synthesis of two particular radiolabelled alkylthiophenyl-guanidine compounds was recently reported by Robins et al (Bioorganic and Medicinal Chemistry Letters, 2010; 20 (5): 1749-51):

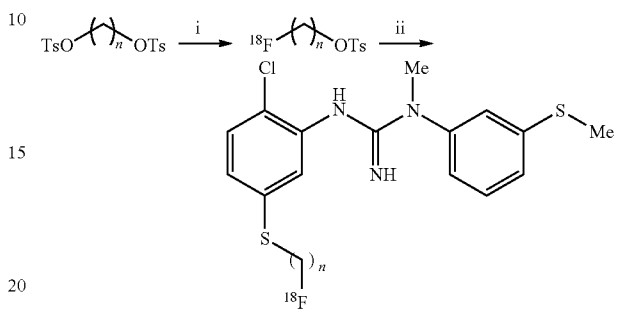

The $^{18}F$-fluoroalkyl tosylate synthons were prepared by reaction in step (i) of the ditosylate starting material with $K^{18}F$/Kryptofix 2.2.2 in acetonitrile at 90° C. for 15 minutes. The labelled guanidine compounds were obtained in step (ii) by alkylation of the associated thiol precursor compound with the relevant $^{18}F$ fluoroalkyl tosylate synthon in acetonitrile in the presence of the base $Cs_2CO_3$. The present inventors have observed an acetyl impurity generated on carrying out the above step (ii):

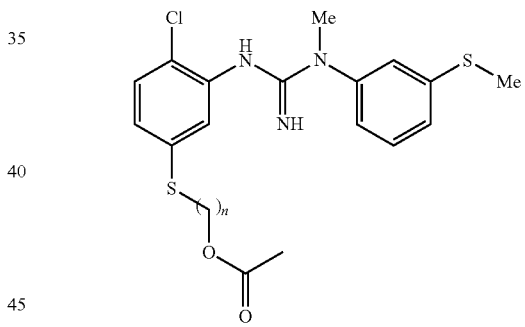

This acetyl impurity was found to be difficult to remove from the crude reaction mixture by HPLC, resulting in an overly-long and complicated radiosynthesis.

Another example of an $^{18}F$-fluoroalkylation reaction to obtain a PET tracer is the reaction described by Wang et al (2006 J Radioanalyt Nuc Chem; 270(2): 439-43) used to obtain the $^{18}F$-labeled amino acid O-(2-[$^{18}F$]fluoroethyl)-L-tyrosine ([$^{18}F$]FET):

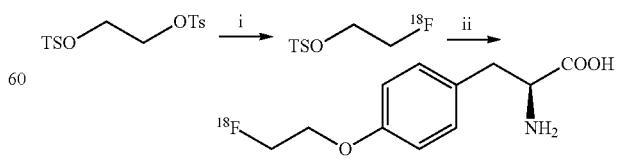

[$^{18}F$]Fluoroethyl tosylate was prepared in step (i) by displacement of a tosyl group from 1,2-bistosyloxyethane by reaction with $K^{18}F$/Kryptofix 2.2.2 in acetonitrile at 90° C.

for 10 minutes. The purified [$^{18}$F]fluoroethyl tosylate was then reacted in step (ii) with a solution of L-tyrosine and 10% aqueous NaOH in DMSO (or di-Na-salt of L-tyrosine in DMSO) 20 minutes at 90° C. to obtain [$^{18}$F]FET. In contrast to the method for preparation of $^{18}$F-labelled S-fluoroalkyl diarylguanidines as reported by Robins et al (supra), this method for preparation of [$^{18}$F]FET uses a soluble base in the alkylation reaction. However, the reaction is still not ideal for carrying out on an automated synthesis device that uses a cassette due to the fact that and additional vial is required for the base used for the subsequent fluoroalkylation step.

Lundkvist et al (1997 Nuc Med Biol; 24: 621-7) describe the synthesis of [$^{18}$F]fluoropropyl-β-CIT (β-CIT: (−)-2β-Carbomethoxy-3β-(4-iodophenyl)tropane) using the [$^{18}$F] fluoropropyl bromide as the labelling reagent. In step (i) [$^{18}$F]fluoropropyl bromide was prepared by a nucleophilic fluorination of 1,3-dibromopropane with [$^{18}$F] potassium Kryptofix complex. [$^{18}$F]Fluoropropyl bromide in dimethyl formamide (DMF) was then used in step (ii) to alkylate nor-β-CIT at 130° C. for 25 minutes to form [$^{18}$F]fluoropropyl-β-CIT.

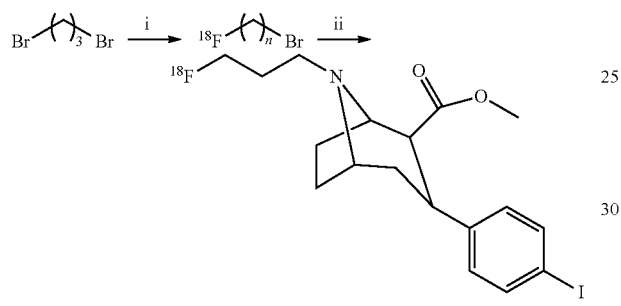

The above method is not ideal for automation since it requires the purification of the synthon via distialltion and an additional reagent vial for the base.

There is therefore a need for a method to obtain the above-described and similar $^{18}$F-labelled compounds that overcomes the various problems and renders the methods more amenable to automation.

SUMMARY OF THE INVENTION

The present invention provides a method for the synthesis of $^{18}$F-labelled biomolecules, which is amenable to automation. The present invention also provides a cassette for automating the method of the invention. The method of the present invention provides numerous advantages over the prior art methods. It requires one less purification step as compared with known methods. Furthermore, in a preferred embodiment it makes use of a particular reagent in two steps thereby minimises the number of reagent vials required. The chemistry process is thereby simplified, the cost of goods is reduced and the burden of validation and documentation of reagents required for GMP clinical production is minimised.

DETAILED DESCRIPTION OF THE INVENTION

Figure 1:
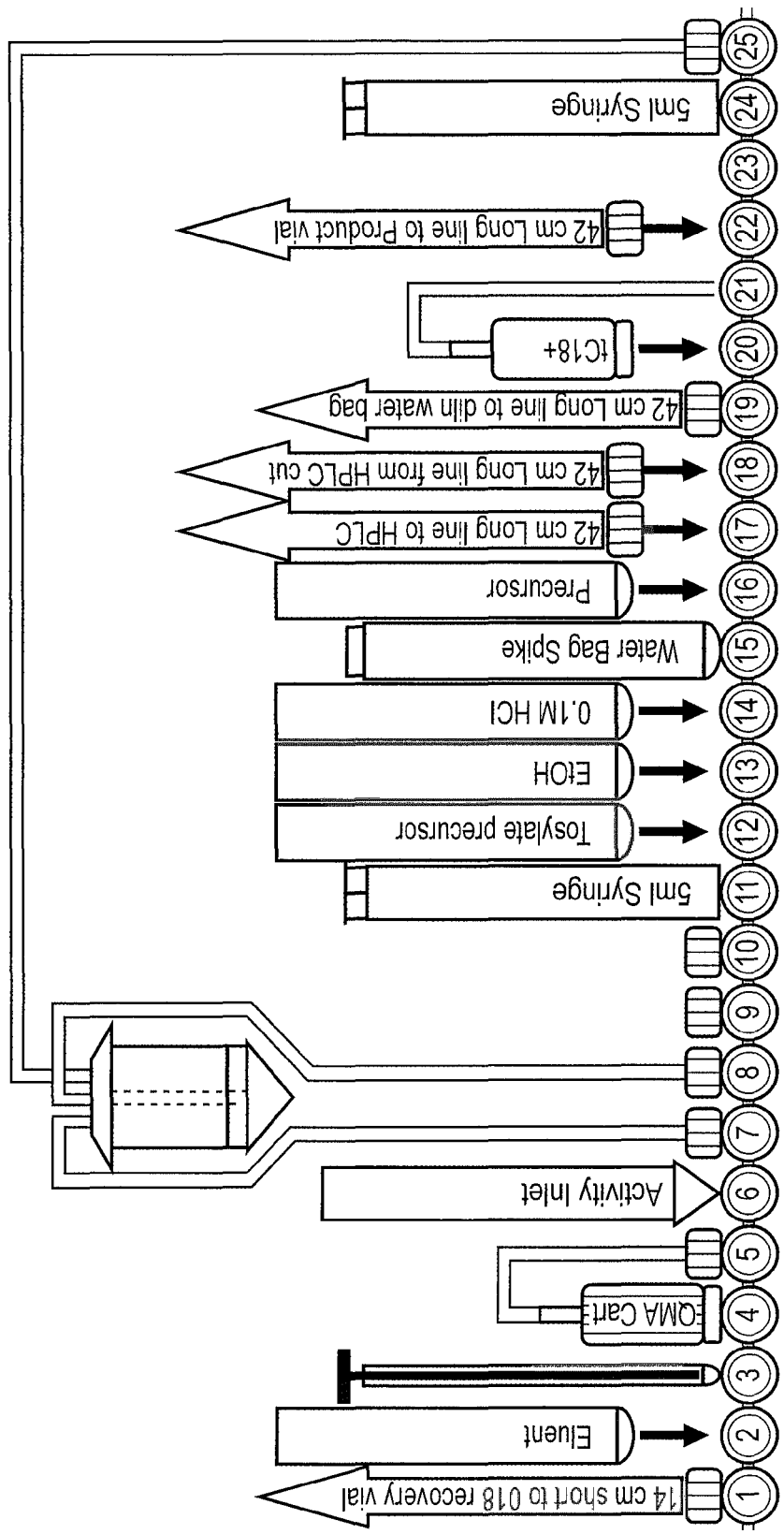
FIG. 1 is a schematic diagram of a cassette as described in example 1.

In one aspect, the present invention provides a method to prepare a compound of Formula I:

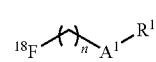

or a salt of a solvate thereof, wherein:

$R^1$-A- is a deprotonated radical of a biological targeting molecule (BTM) of formula $R^1$-A-H wherein A is selected from S, O or $NR^2$ wherein $R^2$ is hydrogen, $C_{1-6}$ alkyl, or $C_{5-12}$ aryl, and, n is an integer of 1-6;

wherein said method comprises:

(i) reacting in a suitable solvent a compound of Formula II:

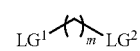

wherein:

$LG^1$ and $LG^2$ are the same or different and each represents a leaving group LG; and, and m is an integer of between 1-4;

with a suitable source of [$^{18}$F]fluoride to obtain a first crude reaction product comprising said compound of Formula II and a compound of Formula III:

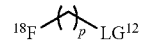

wherein $LG^{12}$ is a leaving group LG and p is as defined for m of Formula II;

(ii) deprotonating a compound of Formula IV.

or a protected version thereof, wherein -$A^2$-$R^{11}$ is as defined for -$A^1$-$R^1$ of Formula I;

(iii) reacting in an alkanol solvent said first crude reaction product obtained in step (i) with said deprotonated compound obtained in step (ii) to obtain a second crude reaction product comprising said compound of Formula I, or a protected version thereof; and, (iv) removing any protecting groups.

A suitable "salt" according to the invention may be selected from (i) physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methane-sulphonic, and para-toluenesulphonic acids; and (ii) physiologically acceptable base salts such as ammonium salts, alkali metal salts (for example those of sodium and potassium), alkaline earth metal salts (for example those of calcium and magnesium), salts with organic bases such as tri-ethanolamine, N-methyl-D-glucamine, piperidine, pyridine, piperazine, and morpholine, and salts with amino acids such as arginine and lysine.

A suitable "solvate" according to the invention may be formed with ethanol, water, saline, physiological buffer and glycol.

The term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning. The BTM may be of synthetic or natural origin, but is preferably synthetic.

The term "synthetic" has its conventional meaning, i.e. man-made as opposed to being isolated from natural sources e.g. from the mammalian body. Such compounds have the advantage that their manufacture and impurity profile can be fully controlled. The molecular weight of the BTM is preferably up to 3,000 Daltons, more preferably 200 to 2,500 Daltons, most preferably 300 to 2,000 Daltons, with 400 to 1,500 Daltons being especially preferred.

Preferably the BTM is an enzyme substrate, enzyme antagonist, enzyme agonist, enzyme inhibitor or receptor-binding compound, in particular a non-peptide, and preferably is synthetic. By the term "non-peptide" is meant a compound which does not comprise any peptide bonds, i.e. an amide bond between two amino acid residues. When the BTM is an enzyme substrate, enzyme antagonist, enzyme agonist or enzyme inhibitor, preferred such biological targeting molecules of the present invention are synthetic, drug-like small molecules i.e. pharmaceutical molecules. Non-limiting examples of particular such biological targeting molecules are described in more detail hereunder.

The term "alkyl" used either alone or as part of another group is defined as any straight, branched or cyclic, saturated or unsaturated $C_nH_{2n+1}$ group.

The term "aryl" used either alone or as part of another group is defined as any $C_{6-14}$ molecular fragment or group which is derived from a monocyclic or polycyclic aromatic hydrocarbon, or a monocyclic or polycyclic heteroaromatic hydrocarbon.

The "suitable solvent" for use in said reacting step (i) is one in which the reactants are readily soluble and readily react to result in the desired product. Examples include N,N-dimethylformamide (DMF), acetone, dichloromethane (DCM), chloroform, dimethylsulphoxide (DMS), methanol, ethanol, propanol, isopropanol, tetrahydrofuran (THF), or acetonitrile, and aqueous solutions thereof. An "aqueous solution" in the context of the suitable solvent for step (i) preferably means 5-20% water, most preferably 10-15% water. Either aqueous ethanol or aqueous acetonitrile are preferred for reacting step (i), but where aqueous acetonitrile is used it is necessary following said reacting step to remove acetonitrile before using the first crude reaction product in reacting step (iii). Aqueous ethanol is preferred.

The term "leaving group" refers to a molecular fragment that departs with a pair of electrons in heterolytic bond cleavage. A suitable leaving group can be a halo, e.g. selected from chloro, iodo, or bromo, or an aryl or alkyl sulphonate. A preferred leaving group is selected from Cl, Br, I, tosylate (OTs), mesylate (OMs) and triflate (OTf). Preferably $LG^1$ and $LG^2$ are the same.

A "suitable source of [$^{18}$F]fluoride" is [$^{18}$F]fluoride that has been made reactive, typically by drying and addition of a cationic counterion. The step of "drying" said [$^{18}$F]fluoride comprises evaporation of water to result in anhydrous [$^{18}$F] fluoride. This drying step are suitably carried out by application of heat and use of a solvent such as acetonitrile to provide a lower boiling azeotrope. A "cationic counterion" is a positively-charged counterion examples of which include large but soft metal ions such as rubidium or caesium, potassium complexed with a cryptand, or tetraalkylammonium salts. A preferred cationic counterion is a metal complex of a cryptand, most preferably wherein said metal is potassium and wherein said cryptand is Kryptofix 222.

The term "crude reaction product" as used in the context of both the first crude reaction product and the second crude reaction product is taken to mean the product of the reaction that has not been subjected to any purification. The term "purification" refers to any method used to isolate from the crude reaction product that chemical compound which is the desired reaction product. The other chemical compounds are generally referred to as "impurities" Typically, this is done by separating the various chemical compounds present in the crude reaction product from each other by means of techniques well-known to those skilled in the art such as chromatography and solid-phase extraction.

The term "deprotonating" refers to the removal of a proton ($H^+$) from the compound of Formula IV and is carried out using a base. This step facilitates the subsequent alkylation reaction. The "base" can be an inorganic base such as potassium or caesium carbonate, potassium hydroxide, or sodium hydride, or an organic base such as a trialkylamine, for example triethylamine, diisopropylethylamine, or dimethylaminopyridine. In a one preferred embodiment, rather than being a separate reagent, the base used for the deprotonating step is the cationic counterion used in preparing reactive [$^{18}$F]fluoride. This preferred embodiment is particularly suitable for automation because less reagent vials are required.

Suitable "protecting groups" and methods for "removing protecting groups" are well known to those skilled in the art. The use of protecting groups is described in 'Protective Groups in Organic Synthesis', by Greene and Wuts (Fourth Edition, John Wiley & Sons, 2007). The step of removing these protecting groups, if present, is preferably carried out after the alkylation step.

The "alkanol solvent" for reacting step (iii) may be an alkanol or an aqueous alkanol, wherein the term "alkanol" is taken to mean a simple aliphatic alcohol. An "aqueous alkanol" consists of water and an alkanol and in the context of this step (iii) means a solution comprising water. Suitably said alkanol solvent does not comprise any solvents apart from water and alkanol, and in particular does not comprise acetonitrile. Suitable alkanols in the context of the present invention include methanol, ethanol and propanol, with ethanol being most preferred.

Compounds of Formula II can be readily obtained by use or straightforward adaptation of methods described by Block et al (J Label Comp Radiopharm, 1988; 25: 201) or by Neal et al (J Label Comp Radiopharm, 2005; 48 557).

Compounds of Formula IV may be prepared by use or straightforward adaptation of the methods described variously in WO 94/27591, WO 2004/007440, WO 2006/136846, Hu et at (J Med Chem, 1997; 40: 4281-9), Zhao et at (J Label Compd Radiopharm, 2006; 49: 163-70) and Robins et al (Bioorganic and Medicinal Chemistry Letters, 2010; 20 (5): 1749-51).

The indications n, m, p and q are in each instance preferably 1-4, most preferably 1-3 and most especially preferably 1-2.

The alkylation step (iii) may be carried out either at room temperature or at higher temperatures (typically 90-130° C.), and following the removal of any protecting groups, the method can comprise the additional step (v) of purifying said second crude reaction product to obtain purified compound of Formula I. Suitably said purifying is carried out by chromatography or solid-phase extraction (SPE), wherein said chromatography is preferably high-performance liquid chromatography (HPLC).

The method of the present invention has the advantage that it does not require purification of the compound of Formula III for use in the alkylation step.

In a preferred embodiment of the method of the invention said compound of Formula I is a compound of Formula Ia:

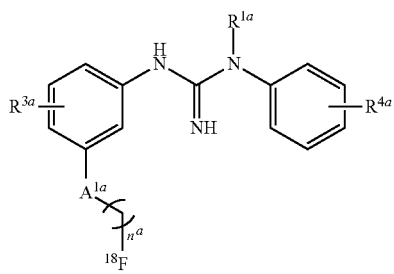

(Ia)

or a salt or solvate thereof, wherein:
$A^{1a}$ is an A group as defined for Formula I,
$R^{1a}$ is an $R^a$ group selected from hydrogen or $C_{1-4}$ alkyl;
$R^{1a}$ is an $R^c$ group which is halo; and
$R^{4a}$ is an $R^d$ group selected from halo, $C_{1-4}$ alkylthio, or $C_{1-4}$ alkyl;
said compound of Formula IV is a compound of Formula IVa:

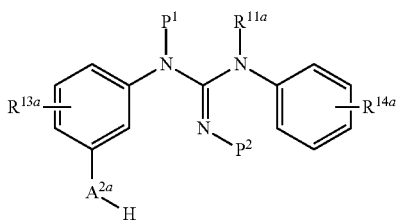

(IVa)

wherein $R^{11a}$, $R^{13a}$ and $R^{14a}$ are respectively an $R^a$, $R^c$ and $R^d$ group as defined for Formula Ia, $A^{2a}$ is an A group as defined for Formula I, and $P^1$ and $P^2$ are each a P group selected from hydrogen or a protecting group, preferably hydrogen.

The term "halogen" or "halo" means a substituent selected from fluorine, chlorine, bromine or iodine.

The term "alkylthio" refers to an alkyl group as defined above comprising a sulphur in the chain, preferably at the proximal end, i.e. —S-alkyl.

Most preferably said compound of Formula Ia is a compound of Formula Ib:

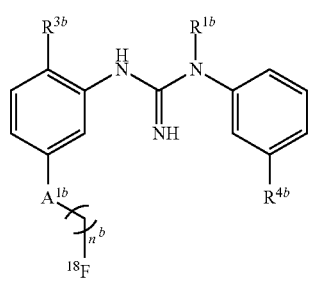

(Ib)

wherein $R^{1b}$, $R^{3b}$, and $R^{4b}$ are respectively an $R^a$, $R^c$ and $R^d$ group as defined for Formula Ia, $A^{1b}$ is an A group as defined for Formula I, and $n^b$ is as defined for n of Formula I;

said compound of Formula IV is a compound of Formula IVb:

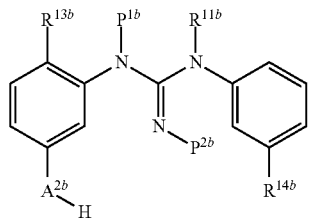

(IVb)

wherein $R^{11b}$, $R^{13b}$, and $R^{14b}$ are respectively an $R^a$, $R^c$ and $R^d$ group as defined for Formula Ia, $A^{2b}$ is an A group as defined for Formula I, and $P^{1b}$ and $P^{2b}$ are each a P group as defined for Formula IVa.

Each $R^a$ group is preferably $C_{1-4}$ alkyl and most preferably methyl.

Each $R^c$ group is preferably chloro.

Each $R^d$ group is preferably alkylthio, and most preferably methylthio.

Each A group is preferably S and $R^{12}$ is preferably SH.

For particular compounds of Formulae Ia and Ib as defined hereinabove it is preferred that:
each $R^a$ group is $C_{1-4}$ alkyl and is most preferably methyl;
each $R^c$ group is chloro;
each $R^d$ group is alkylthio, and is most preferably methylthio; and,
each A group is S and $R^{12}$ is preferably SH; and, Where the method of the invention is for the synthesis of a compound of Formula Ia, the method reported by Robins et al (2010 Bioorg Med Chem Letts; 20: 1749-51) is easily adapted to result in a method of the present invention. This method of Robins et al for the synthesis of $^{18}$F-labelled S-fluoroalkyl diarylguanidines comprises [$^{18}$F]fluoroalkylation of a thiol group using the following method:

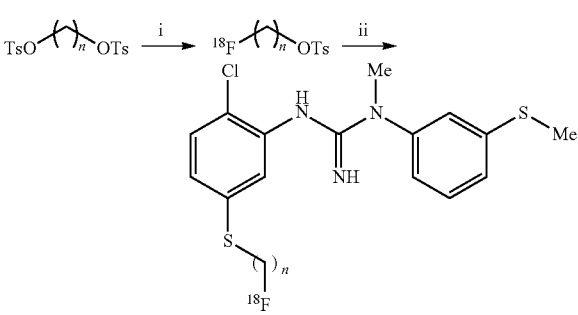

In the above reaction scheme (i) represents OF Kryptofix 2.2.2, MeCN, 90° C., 15 minutes and (ii) represents the thiol derivative of the final product, $Cs_2CO_3$, MeCN, 110° C., 15 minutes. The [$^{18}$F]fluoroalkyltosylate labelling reagent is purified before use in this method of Robins et al. In the method of the present invention the [$^{18}$F]fluoroalkylation step is instead carried out in an aqueous alkanol rather than acetonitrile (MeCN), and the [$^{18}$F]fluoroalkyltosylate labelling reagent is used without having been purified.

A particular advantage of the present method over known methods where the compound of Formula I is a compound of Formula Ia is that purification is made easier by avoiding generation of acetyl impurities in the alkylation step, a problem which was found by the present inventors. The scheme below illustrates the mechanism by which an acetyl impurity is believed to be formed in the synthesis of 3-(2-chloro-5-[18F]fluoroethyl)thio)phenyl)-1-methyl-1-(3-(methylthio)phenyl)guanidine from 3-(2-chloro-5-mercaptophenyl)-1-methyl-1-(3-(methylthio)phenyl)guanidine:

method comprising [18F]fluoroalkylation of a phenol described by Wang et al (2006 J Radioanalyt Nuc Chem; 270(2): 439-43) to obtain the 18F-labeled amino acid O-(2-[18F]fluoroethyl)-L-tyrosine ([18F]FET):

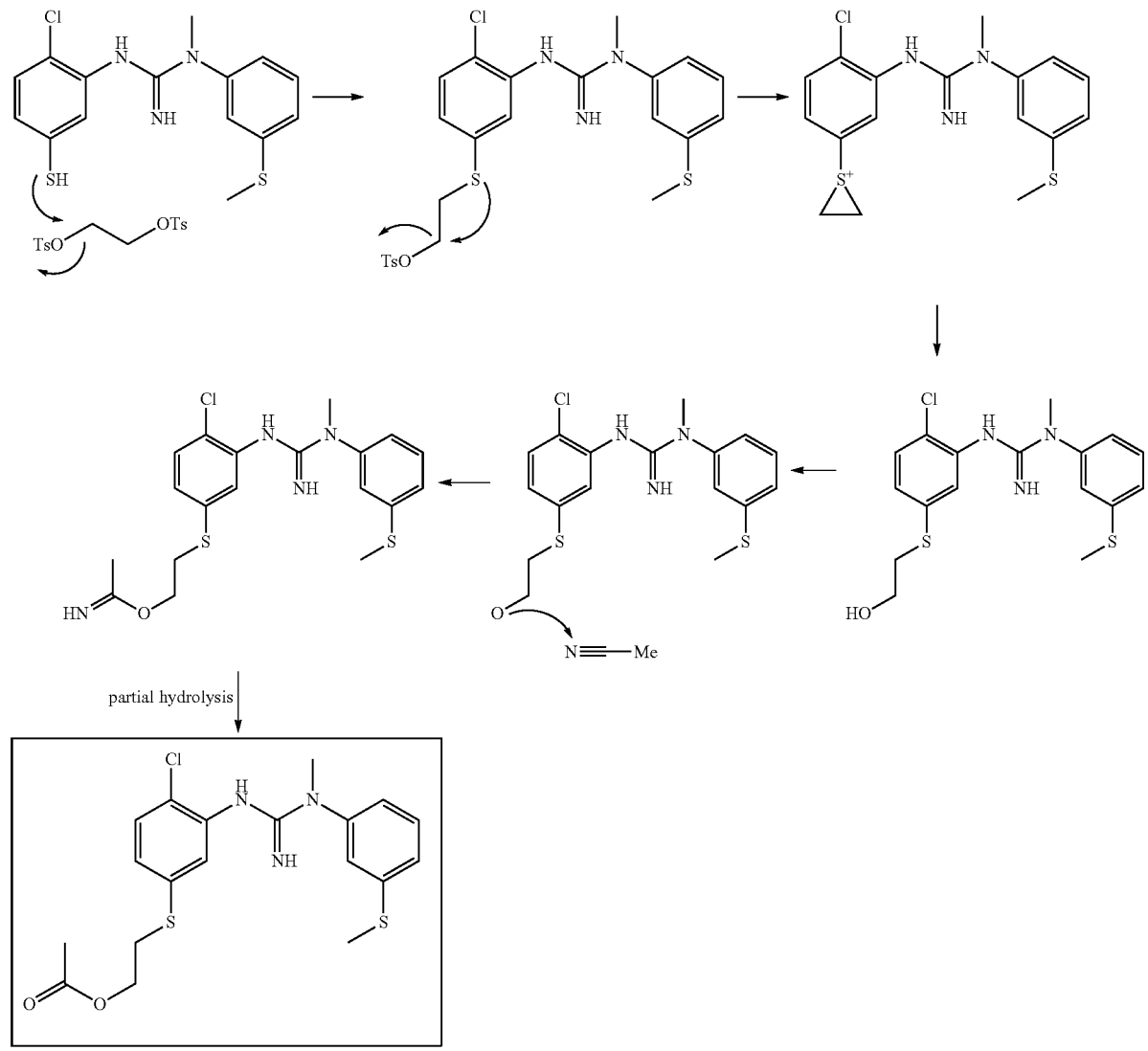

It is proposed that use of alkanol solvent in place of acetonitrile in the [18F]fluoroalkylation step (iii) avoids the production of this acetyl impurity. Furthermore, use of the alkanol solvent in the [18F]fluoroalkylation step means that the first crude reaction product comprising the compounds of Formulae II and III can be used directly in the alkylation without having to purify to remove unreacted compound of Formula II, which would be necessary if acetonitrile were to be used in the [18F]fluoroalkylation step to avoid the reaction illustrated above. When an alkanol solvent is used, any unreacted compound of Formula II can still react with the deprotonated compound of Formula IV, but the impurity generated as a consequence will be a hydroxyl impurity which is straightforward to separate in any subsequent purification step.

Another known method that can be adapted in a straightforward manner to be a method of the present invention is the

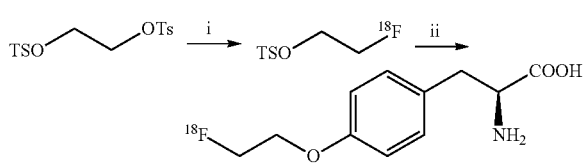

[18F]Fluoroethyl tosylate obtained in step (i) can be reacted in step (ii) (without needing to first be purified) with a solution of L-tyrosine in an aqueous alkanol (rather than DMSO) which has been treated with an aliquot of the solution of K₂CO₃ and Kiyptofix 222 (rather than NaOH) previously used in the method to make reactive [18F][K(Kryptofix)]F for use in step (i).

Accordingly, another example of a preferred compound of Formula IV is the following compound:

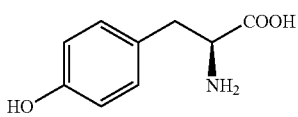 [SMILES: N[C@@H](Cc1ccc(O)cc1)C(=O)O]

In the method described by Lundkvist et al (1997 Nuc Med Biol; 24: 621-7) for the synthesis of [$^{18}$F]fluoropropyl-β-CIT (β-CIT: (−)-2β-Carbomethoxy-3β-(4-iodophenyl)tropane) a secondary amine is alkylated using [$^{18}$F]fluoropropyl bromide:

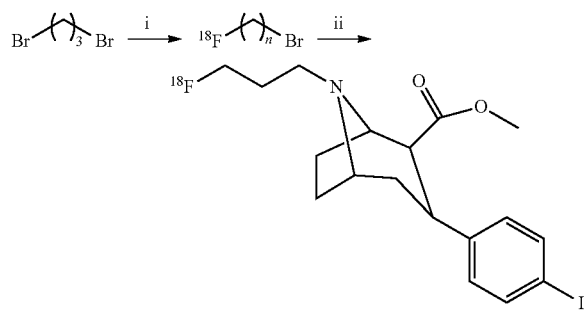

This method can be readily adapted to be a method of the present invention by carrying out step (ii) in an aqueous alkanol solution. Preferably an aliquot of $K_2CO_3$ and Kryptofix 222 (with acetonitrile removed), which is used to make reactive [$^{18}$F][K(Kryptofix)]F in step (i), is used in step (ii) as a base.

Accordingly, another example of a preferred compound of Formula IV is the following compound:

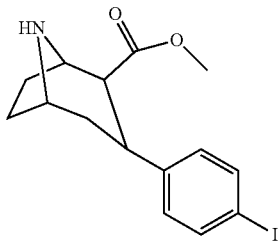 [SMILES: COC(=O)C1C2CCC(CC1c1ccc(I)cc1)N2]

The above-described compounds merely provide illustrations of how the method of the present invention may be applied. It will be clearly appreciated by the skilled person that the method of the present invention can also be applied to achieve similar advantages to any reaction that comprises (i) synthesis of an [$^{18}$F]fluoroalkyl labelling reagent using [$^{18}$F]fluoride as the source of $^{18}$F, and (ii) [$^{18}$F]fluoroalkylation of a thiol, hydroxy or amine functionality in a precursor compound.

The method of the present invention is particularly amenable to automation as compared to known methods. Automation may be carried out on an automated radiosynthesis apparatus. There are several commercially-available examples of such apparatus, including Tracerlab MX™ and FASTlab™ (GE Healthcare), FDGPlus Synthesizer (Bioscan) and Synthera® (IBA). Such apparatus may comprise a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. As the method of the present invention does not require purification of the first crude reaction product, and as the second crude reaction product is relatively easy to purify, the method of the present invention is amenable to automation. Therefore, in a preferred embodiment, the method of the present invention is automated, most preferably by means of a cassette on an automated radiosynthesis apparatus. The present invention therefore provides in another aspect a cassette for the automated synthesis of the compound of Formula I as defined herein wherein said cassette comprises:

(i) a first vessel containing a compound of Formula II as defined herein;
(ii) means for eluting said first vessel with a suitable source of [$^{18}$F]-fluoride; and,
(iii) a second vessel containing a compound of Formula IV as defined herein.

The suitable and preferred embodiments of the compounds of Formulae II and IV, and the suitable source of [$^{18}$F]fluoride as defined hereinabove for the method of the present invention are also applicable to the cassette of the present invention.

The term "vessel" is taken to mean a reagent vial suitable for placing in a position on a cassette suitable for use with an automated radiosynthesis apparatus.

Additional vessels may be present specific to the chemistry/biomolecule synthesis e.g. vials for solvents for deprotection, purification, formulation, reformulation. Additional cartridges (SPE) may also be present for purification and/or re-formulation. There may also be a connection line from the cassette to a HPLC unit if HPLC purification is required, and there may be a connection line from the "HPLC cut vial" to the cassette if there is a requirement for solvent reformulation post purification.

Therefore in another embodiment, the cassette of the present invention may additionally comprise either or both of:

(iv) an ion-exchange cartridge for removal of excess [$^{18}$F] fluoride; and,
(v) a cartridge for carrying out the step of removing any protecting groups.

The reagents, solvents and other consumables required for the automated synthesis may also be included together with a data medium, such as a compact disc carrying software, which allows the automated synthesiser to be operated in a way to meet the end user's requirements for concentration, volumes, time of delivery etc.

BRIEF DESCRIPTION OF THE EXAMPLES

Example 1 describes the automated synthesis of 3-(2-chloro-5-((2-[$^{18}$F]fluoroethyl)thio)phenyl)-1-methyl-1-(3-(methylthio)phenyl)guanidine using the method of the present invention.

Example 2 describes an experiment comparing FASTlab™ synthesis of 3-(2-chloro-5-((2-[$^{18}$F]fluoroethyl)thio)phenyl)-1-methyl-1-(3-(methylthio)phenyl)guanidine using ethanol or acetonitrile as the solvent.

LIST OF ABBREVIATIONS USED IN THE EXAMPLES

EtOH ethanol
HPLC high performance liquid chromatography
$K_{222}$ Kryptofix 2.2.2
MeCN acetonitrile
QMA quaternary methylammonium
SPE solid phase extraction
TsO tosylate

EXAMPLES

Example 1

FASTlab™ Synthesis of 3-(2-chloro-5-((2-[$^{18}$F]fluoroethyl)thio)phenyl)-1-methyl-1-(3-(methylthio)phenyl)guanidine A cassette for use with a FASTlab™ synthesiser comprised the following vials:

| Vial number | Vial name | Composition |
| --- | --- | --- |
| 1 | Eluent | $K_{222}$ = 53 mg/mL; $K_2CO_3$ 9.5 mg/mL<br>Solvent: (12.5% water, 87.5% EtOH) |
| 2 | TsO(CH$_2$)$_2$OTs | Ethylene ditosylate (4.0 mg)<br>MeCN (1.6 mL) |
| 3 | EtOH | EtOH (4.0 mL) |
| 4 | HCl | 0.1M HCl (4 ml) |
| 5 | Precursor | Precursor* (15 mg)<br>EtOH (1.8 mL)) |

*3-(2-chloro-5-mercaptophenyl)-1-methyl-1-(3-methylthio)phenyl)guanidine

The cassette is also illustrated in FIG. 1.

1(i) Transfer of [$^{18}$F]fluoride to Cassette

[$^{18}$F]Fluoride was supplied from GE Healthcare on a GE PETrace cylcotron. The initial activity was transferred via the activity inlet of the FASTlab cassette using vacuum.

1(ii) Trapping [$^{18}$F]fluoride on the QMA

The activity was transferred from the activity inlet to the (pre-treated) QMA cartridge where the [$^{18}$F] was trapped and the water passed through to the $^{18}$O water recovery vial, using a combination of $N_2$ to push and vacuum to pull.

1(iii) Elution of [$^{18}$F]Fluoride off the QMA

70 µL of the eluent vial ($K_{222}$, $K_2CO_3$) was removed from the eluent vial using the 1 mL syringe. 550 µL of water was then withdrawn from the water bag and added to the eluent in the 1 mL syringe. The [$^{18}$F]fluoride trapped on the QMA cartridge was then eluted into the reaction vessel using the eluent/water solution in the 1 mL syringe and a vacuum applied to the reaction vessel to draw the solution through the QMA cartridge.

1(iv) Drying [$^{18}$F]fluoride

The [$^{18}$F]fluoride and eluent solution was dried for 20 minutes by heating (100° C.) and a combination of nitrogen and vacuum were used to remove the evaporated solvent and water from the reaction vessel to a waste collection vessel.

1(v) Radiosynthesis of [$^{18}$F]-fluoroethyltosylate 1 mL of the ethylene ditosylate solution (2.5 mg per mL of MeCN) was removed from the vial using the centre (5 ml) syringe and dispensed into the reaction vessel containing the dried [$^{18}$F]fluoride/K222/$K_2CO_3$ (reactive [$^{18}$F][K(Kryptofix)]F). The reaction vessel was then sealed and the reaction carried out by heating for 15 minutes at 86° C.

1(vi) Removal of Solvent from the [$^{18}$F]-fluoroethyltosylate

The crude [$^{18}$F]-fluoroethyltosylate/ethylene ditosylate solution was dried for 10 minutes by heating (80° C.) and a combination of nitrogen and vacuum was used to remove the evaporated solvent from the reaction vessel to a waste collection vessel.

1(vii) Introduction of 500 µL of Eluent to Precursor Vial

500 µL of eluent vial ($K_{222}$, $K_2CO_3$) was removed from the eluent vial and added into the precursor vial using the 1 mL syringe. The solution was held for 1 minute.

1(viii) Introduction of Precursor to Reaction Vessel 10 mg (26 µmol) of precursor 3-(2-chloro-5-mercaptophenyl)-1-methyl-1-(3-(methylthio)phenyl)guanidine) in 1.5 mL of ethanol was removed from the vial by creating a vacuum in the reaction vessel.

1(ix) Alkylation of Precursor

The reaction vessel was then sealed and the alkylation carried out by initially heating for 2 minutes at 80° C., then 13 minutes at 100° C.

1(x) Loop Flush Out with Water

A total of 10 mL water was removed from the water bag using the centre (5 ml) syringe and sent through the HPLC loop in two syringe movements.

1(xi) Quench Reaction, and Transfer Out of FASTlab to HPLC Loop 2 mL water was added to the reaction vessel from the water bag using the centre 5 mL syringe. 1 mL 0.1M HCl was added to the reaction vessel from the vial using the centre 5 mL syringe. This was then withdrawn from the reaction vessel using the same syringe and transferred from the cassette to the HPLC loop, followed by a purge of the line and cassette fluid path with nitrogen to clear any residual solution to the HPLC loop.

1(xii) HPLC Purification and SPE Formulation

The following HPLC method was used:

| | |
| --- | --- |
| 0-60 mins | 40% (B) |
| Column | ACE C18 100 × 10 mm 5 µm |
| Mobile phase | Mobile phase A (pump A): Acetonitrile (pump B) |
| Loop Size | 10 ml |
| Pump speed | 3 ml/min |
| Wavelength | 254 nm |
| Mobile Phase A: | 0.8% TEA [TEA (8 ml) and H2O (992 ml)], pH adj to ca. 7.5 with 85% H3PO4 (ca. 2.1 ml) |

The HPLC run was controlled from the HPLC software until the cut was performed. The HPLC cut was transferred back to the FASTlab using the right hand (5 ml) syringe to draw the cut back on to the cassette then add to the dilution water bag. The diluted HPLC cut (>100 mL) was loaded on to a tC18+ SPE cartridge by applying a vacuum for 11 minutes to draw the full content of the water bag through the cartridge to a waste collection vessel. The SPE cartridge was eluted with 1 mL ethanol from the vial using the right hand 5 mL syringe into a vial containing 14 mL saline containing 1.5 mg ascorbic acid.

In summary, the following were observed:

| | |
| --- | --- |
| Average yield (MBq)<br>(starting from 37 GBq of [1$^8$F]fluoride) | 3177 |
| Average RCP (%) | 97 |
| Average Specific Activity (GBq/µmole) | 581 |
| Number of production runs | 23 |

Example 2

Comparison of FASTlab™ Synthesis of 3-(2-chloro-5-((2-[$^{18}$F]fluoroethyl)thio)phenyl)-1-methyl-1-(3-(methylthio)phenyl)guanidine using Ethanol or Acetonitrile as the Solvent The process described in Example 1 was carried out up to step 1(xi) but wherein the following step was analytical HPLC using the following method:

Mobile Phase A. 0.8% TEA (8 mL TEA and 992 mL H$_2$O), pH adj. to ca. 7.5 with 85% H$_3$PO$_4$ (ca. 2.1 mL)

Mobile phase B: MeCN 0-1 min 40% B; 1-25 min 40-95% B

HPLC column: Luna C18 (150×4.6 mm)

Flow rate: 1 mL/min

Figure 2:
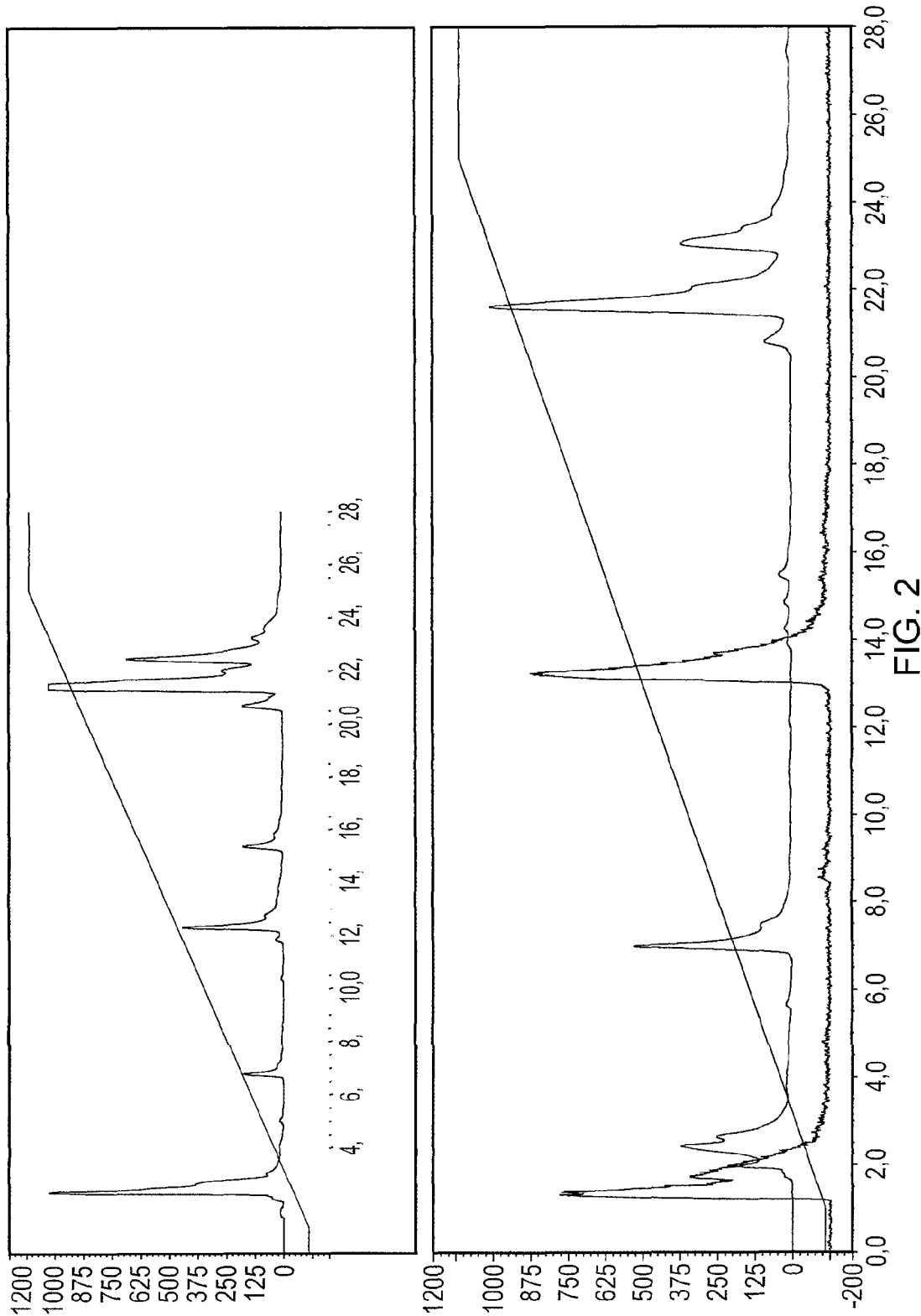
FIG. 2 is a graphic comparison of synthesis using acetonitrile (top) and ethanol (bottom) as solvent.

In addition, the same process was carried out wherein acetonitrile was used as the solvent in place of ethanol. FIG. 2 compares the synthesis wherein acetonitrile (top) was used in place of ethanol (bottom) as the solvent. It can be clearly seen that the acetyl chemical impurity that elutes around 12 minutes (with product eluting just afterwards) is not formed when acetonitrile has been removed from the alkylation step.

What is claimed is:

1. A method to prepare a compound of Formula I:

or a salt of a solvate thereof, wherein:
$R^1$-A- is a deprotonated radical of a biological targeting molecule (BTM) of formula $R^1$-A-H wherein A is selected from S, O or $NR^2$ wherein $R^2$ is hydrogen, $C_{1-6}$ alkyl, or $C_{5-12}$ aryl; and,
n is an integer of 1-6;
wherein said method comprises:
(i) reacting in a suitable solvent a compound of Formula II:

wherein:
$LG^1$ and $LG^2$ are the same or different and each represents a leaving group LG; and,
and m is an integer of between 1-4;
with a suitable source of [$^{18}$F]fluoride to obtain a first crude reaction product comprising said compound of Formula II and a compound of Formula III:

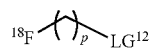

wherein $LG^{12}$ is a leaving group LG and p is as defined for m of Formula II;
(ii) deprotonating a compound of Formula IV:

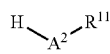

or a protected version thereof, wherein -$A^2$-$R^{11}$ is as defined for -$A^1$-$R^1$ of Formula I;
(iii) reacting in an alkanol solvent said first crude reaction product obtained in step (i) with said deprotonated compound obtained in step (ii) to obtain a second crude reaction product comprising said compound of Formula I, or a protected version thereof; and,
(iv) removing any protecting groups.

2. The method as defined in claim 1 wherein:
said compound of Formula I is a compound of Formula Ia:

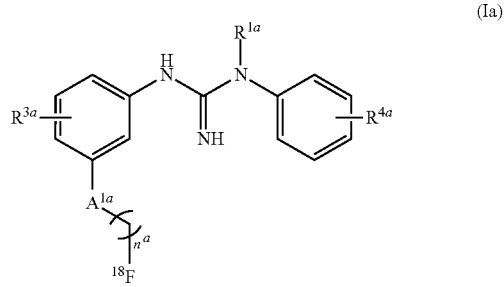

or a salt or solvate thereof, wherein:
$A^{1a}$ is an A group as defined for Formula I;
$R^{1a}$ is an $R^a$ group selected from hydrogen or $C_{1-4}$ alkyl;
$R^{3a}$ is an $R^c$ group which is halo; and
$R^{4a}$ is an $R^d$ group selected from halo, $C_{1-4}$ alkylthio, $C_{1-4}$ alkyl;
said compound of Formula IV is a compound of Formula IVa:

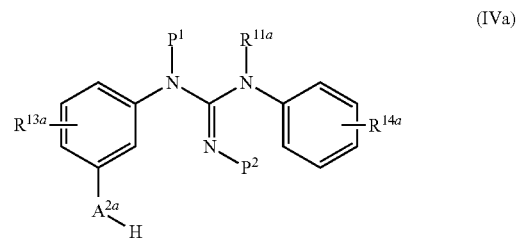

wherein $R^{11a}$, $R^{13a}$, and $R^{14a}$ are respectively an $R^a$, $R^c$ and $R^d$ group as defined for Formula Ia, $A^{2a}$ is an A group as defined for Formula I, and $P^1$ and $P^2$ are each a P group selected from hydrogen or a protecting group.

3. The method as defined in claim 2 wherein:
said compound of Formula I is a compound of Formula Ib:

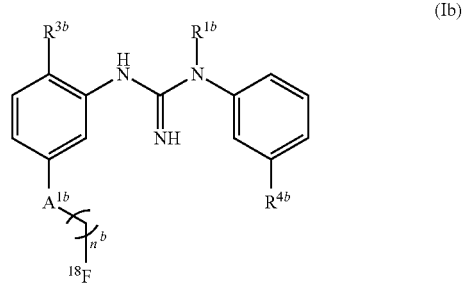

wherein $R^{1b}$, $R^{3b}$, and $R^{4b}$ are respectively an $R^a$, $R^c$ and $R^d$ group as defined in claim 2 for Formula Ia, $A^{1b}$ is an A group as defined for Formula I, and $n^b$ is as defined for n of Formula I;

said compound of Formula IV is a compound of Formula IVb:

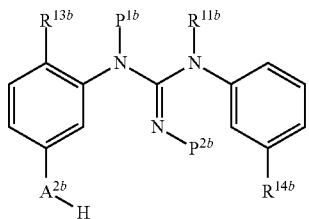
(IVb)

wherein $R^{11b}$, $R^{13b}$, and $R^{14b}$ are respectively an $R^a$, $R^c$ and $R^d$ group as defined in claim 2 for Formula Ia, $A^{2b}$ is an A group as defined for Formula I, and $P^{1b}$ and $P^{2b}$ are each a P group as defined in claim 2 for Formula IVa.

4. The method as defined in claim 2 wherein each $R^a$ group is $C_{1-4}$ alkyl.

5. The method as defined in claim 4 wherein each $R^a$ group is methyl.

6. The method as defined in claim 2 wherein each $R^c$ group is chloro.

7. The method as defined in claim 2 wherein each $R^d$ group is alkylthio.

8. The method as defined in claim 7 wherein each $R^d$ group is methylthio.

9. The method as defined in claim 2 wherein said A group is S.

10. The method as defined in claim 1 wherein said compound of Formula IV is the following compound:

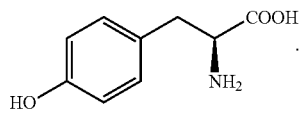 [SMILES: N[C@@H](Cc1ccc(O)cc1)C(=O)O]

11. The compound as defined in claim 1 wherein said compound of Formula IV is the following compound:

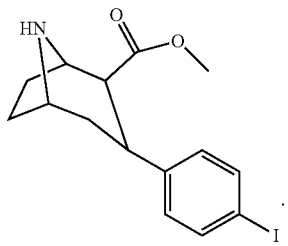 [SMILES: COC(=O)C1C2CCC(CC1c1ccc(I)cc1)N2]

12. The method as defined in claim 1 wherein said leaving group LG is selected from Cl, Br, I, tosylate (OTs), mesylate (OMs) and triflate (OTf).

13. The method as defined in claim 1 wherein $LG^1$ and $LG^2$ are the same.

14. The method as defined in claim 1 which comprises the additional step (v) of purifying said second crude reaction product to obtain purified compound of Formula I.

15. The method as defined in claim 1 which is automated.

* * * * *